United States Patent [19]

Gardner et al.

[11] 4,454,321

[45] Jun. 12, 1984

[54] PREPARATION OF AMINES FROM OLEFINS USING CERTAIN TRANSITION METAL CATALYSTS

[75] Inventors: David M. Gardner, Collegeville; Roger T. Clark, Pottstown, both of Pa.

[73] Assignee: Pennwalt Corporation, Philadelphia, Pa.

[21] Appl. No.: 387,625

[22] Filed: Jun. 11, 1982

Related U.S. Application Data

[63] Continuation-in-part of Ser. No. 143,985, Apr. 28, 1980, abandoned.

[51] Int. Cl.³ .................... C07C 85/02; C07D 211/00
[52] U.S. Cl. .................................. 546/184; 564/408; 564/485
[58] Field of Search ................ 564/408, 485; 546/184

[56] References Cited

U.S. PATENT DOCUMENTS

| | | | |
|---|---|---|---|
| 3,412,158 | 11/1968 | McClain et al. | 564/485 |
| 3,600,413 | 8/1971 | Grimm | 564/485 X |
| 3,758,586 | 9/1973 | Coulson | 564/485 |
| 4,204,997 | 5/1980 | Hobbs et al. | 564/408 X |
| 4,215,218 | 7/1980 | Diamond et al. | 564/408 X |

OTHER PUBLICATION

Fieser et. al. "Reagents for Organic Synthesis" Vol. 3, Page 242 (1972)

*Primary Examiner*—Robert V. Hines

[57] ABSTRACT

Aliphatic and aromatic amines are produced by reacting an olefin with either ammonia or a primary or secondary amine in the presence of a catalytic amount of ruthenium or iron compound catalyst. The reaction is carried out in the liquid phase using an inert liquid, a product amine, or one of the reactants as a solvent. The temperatures used are 100° to 250° C. and the pressures are at least autogenous and up to 12,000 psig.

9 Claims, No Drawings

PREPARATION OF AMINES FROM OLEFINS USING CETAIN TRANSITION METAL CATALYSTS

BACKGROUND OF THE INVENTION

This application is a continuation-in-part of copending Ser. No. 143,985 filed Apr. 28, 1980 and now abandoned.

This invention relates to the preparation of aliphatic and aromatic amines by a catalytic reaction in the liquid phase of an olefin with ammonia or a primary or secondary amine. More particularly, this invention relates to the preparation of amines in the presence of a catalyst which is a simple salt or a coordination compound of ruthenium or iron.

U.S. Pat. No. 3,412,158 describes the reaction of ammonia with olefins in the vapor phase over a catalytic amount of a Group VIII noble metal or the salts or oxides thereof, to produce the corresponding aliphatic amines.

U.S. Pat. No. 3,758,586 discloses that in the presence of certain coordination compounds of rhodium, secondary amines and ethylene react catalytically in the liquid phase to give free tertiary amines. It is also disclosed that ammonia and primary amines are ineffective in this reaction, and that the reaction is operative only with ethylene.

No prior art was found that suggests that either ruthenium or iron salts or coordination compounds could be used to catalyze the liquid phase reaction of an olefin and ammonia or an amine whereby an N—H bond is added across the double bond of the olefin. Ruthenium and iron compounds are commercially attractive catalysts because they are less expensive than platinum, palladium, or rhodium compounds.

STATEMENT OF THE INVENTION

This invention is directed to a process for the production of aliphatic and aromatic amines which comprises reacting, in a liquid phase, an olefin of from 2 to 18 carbon atoms with either ammonia, a lower primary amine or a lower secondary amine in the presence of a catalyst at a temperature of 100° to 250° C. and at a pressure which is at least autogenous and up to 12,000 psig whereby an N—H bond is added across the double bond of the olefin, said catalyst being selected from the group consisting of
(i) a ruthenium or iron salt and
(ii) a coordination compound of ruthenium or iron.

DEFINITIONS

The present invention can be described by the equation:

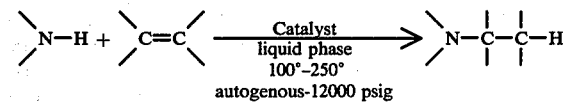

The above equation indicates that an N—H bond adds across the double bond of an olefin.

Suitable amines for this invention include ammonia and lower primary and lower secondary amines. By lower amines is meant those aliphatic, cyclic and aromatic amines having not more than 6 carbon atoms such as methylamine, ethylamine, aniline, dimethylamine, diethylamine, piperidine, and other similar amines. A preferred amine is ammonia.

By "olefins" is meant compounds having one or more isolated (i.e., non-conjugated) double bonds. Preferred olefins are $C_2$–$C_8$ alkyl α-olefins. Particularly preferred are $C_2$–$C_4$ olefins such as ethylene, propylene, butylene, and isobutylene. Especially preferred is ethylene.

By "liquid phase" is meant that the reactants and catalyst are either liquids or dissolved in a liquid which may be one of the reactants, a product amine or an inert liquid which functions as a solvent for the reactants and the catalyst during the reaction. Typical examples of these optional inert liquid solvents are: saturated aliphatic hydrocarbons, such as hexane, heptane and cyclohexane; aromatic hydrocarbons, such as toluene, xylene and benzene; ethers such as tetrahydrofuran, 1,4-dioxane and ethylene glycol monomethylether; and saturated aliphatic alcohols, such as methanol and ethanol.

Temperatures in the range of 100° to 250° C. are useful for carrying out this invention. The preferred temperature range is 100° to 190° C.

Pressures in the range of at least autogenous and up to 12,000 psig are useful for carrying out this invention. Pressures in the range of 200 psig to 1500 psig are preferred.

The amounts of olefin and amine which are reacted together in this process are not critical but, in preferred use, the reactants are present in a ratio of from 0.1 to 10 moles of amine per mole of olefin. The amount of amine present in the reaction in excess of stoichiometric can function as a solvent for the reaction.

The catalyst is used in a ratio ranging from about 0.005 to 10 mole per mole of olefin or amine, whichever reactant is used in the lesser molar amount. Preferably, the amount of catalyst is kept as low as possible and yet is used in an amount sufficient to provide good yields and kinetics, i.e., from 0.01 to 1 mole per mole of the lesser amount of reactant employed.

The catalyst is a simple salt of either ruthenium or iron or a coordination compound of either ruthenium or iron. The preferred ruthenium and iron salts are salts of strong mineral acids or organic acids. Specific examples of such salts include chloride, bromide, iodide, nitrate, sulfate, phosphate, formate, and acetate salts and their hydrates.

The preferred coordination compounds of ruthenium are:
$RuCl_2(triphenylphosphine)_3$;
$Ru(cyclopentadienyl)_2$;
$Ru(2,4-pentanedionate)_3$;
$Ru(dimethylglyoxime)_2Cl$;
$Ru(2-cyanopyridine)_2Cl$;
$Ru(triphenylarsine)_2Cl_3$,
$Ru(N,N-ethylene-bis-salicylideneamine)Cl_3$;
$Ru(8-hydroxyquinoline)_2Cl$;
$Ru(2-hydroxyquinoline)_2Cl$;
$Ru(dimethylglyoxime)_4Cl_2$;
$Ru(2,2'-bipyridine)_2Cl$;
$K_4Ru(CN)_6.3H_2O$;
$[Ru(NH_3)_4OHCl]Cl.2H_2O$;
$Ru(NO)(NO_3)_3$ The preferred coordination compounds of iron are:
$Fe(CO)_5$
$Fe_2(CO)_9$
$Fe(butadiene)(CO)_3$
$HgCl(cyclopentadienyl)_2Fe$ $H_2Fe(CO)_4$
Fe(cyclohexadienyl)$(CO)_3$
$FeHg(CO)_4$
$Fe(CO)_4[(C_6H_5)_3P]$
$Fe(CO)_4[(C_6H_5O)_3P]$ The process of this invention may be carried out on a batch basis, or is equally adaptable to a continuous basis by employing known means for introducing the reactants, catalyst, and optional solvent to the reaction zone and for withdrawing the products and recovering starting materials therefrom. As indicated by the low molar percentage of catalyst to reactants, the reaction is truly catalytic rather than stoichiometric in nature.

EXAMPLES

The following examples illustrate various embodiments of this invention. Parts and percentages are by weight, temperatures are in degrees Centigrade, and pressures are in pounds per square inch gauge unless otherwise specified. Conversions and yields given in these examples are based on the isolated liquid products. Major products were identified by gas chromatographic and mass spectroscope analytical methods, and when necessary, were confirmed by infrared spectroscopy. Those minor products which are not identified are assumed to have the same gas chromatographic response factor as the major amine product.

In Examples 1–4, 6 and 7 the temperature-time profile during the reactions was 150° C. (1st hour), 170° C. (2nd hour) and 190° C. (next 5 hours). In Examples 5, 10 and 11 the temperature-time profile was 150° C. (1st hour) and 170° C. (next 5 hours). These periodic changes in reaction temperatures are not critical to the process and were made for experimental purposes only. In the remaining examples the temperature of the reaction is as stated therein.

In each of the following examples the reaction occurs in the liquid phase where either the reactants and catalyst are dissolved in an inert solvent or one reactant and the catalyst are dissolved in a solvent reactant.

In all test runs it has been observed that no products are formed in either the absence of catalyst or in the presence of an ineffective catalyst.

EXAMPLE 1

A mixture of 89 parts of tetrahydrofuran (inert solvent), 5.6 parts of dimethylamine and 0.315 parts (0.011 mol/mol $C_2H_4$) of ruthenium trichloride hydrate were placed in a 300 ml stainless steel autoclave. The autoclave was pressured with 10 psig of hydrogen and 200 psig of ethylene. A total of 0.16 parts of dimethylethylamine and 3.3 parts of diethylmethyl amines were obtained corresponding to a conversion of 35% and a combined yield of 92%.

EXAMPLE 2

A mixture of 89 parts of tetrahydrofuran (inert solvent), 5.6 parts of dimethylamine and 0.289 parts (0.011 mol/mol $C_2H_4$) of Ru(cyclopentadienyl)$_2$ were placed in a 300 ml stainless steel autoclave. The autoclave was pressured with 200 psig of ethylene. A total of 1.3 parts of dimethylethylamine were obtained corresponding to a conversion of 1% and a yield of 99% (based on dimethylamine).

EXAMPLE 3

A mixture of 104 parts of 1,4-dioxane (inert solvent), 5.6 parts of dimethylamine and 0.363 parts (0.11 mol/mol $C_2H_4$) of [Ru(NH_3)_4(OH)Cl]Cl.2H_2O were placed in a 300 ml stainless steel autoclave. The autoclave was pressured with 200 psig of ethylene. A total of 0.12 parts of dimethylethylamine and 2.1 parts of diethylmethylamine were obtained corresponding to a conversion of 21% and a combined yield of 99% (based on dimethylamine).

EXAMPLE 4

A mixture of 104 parts of 1,4-dioxane (inert solvent), and 0.315 parts (0.011 mol/mol $C_2H_4$) of ruthenium trichloride hydrate were placed in a 300 ml stainless steel autoclave. The autoclave was pressured with 200 psig of anhydrous ammonia and 200 psig of ethylene. The resulting reaction mixture was analyzed by gas liquid chromatography and was found to contain monoethylamine, diethylamine, and triethylamine.

EXAMPLE 5

A mixture of 18.3 parts of anhydrous diethylamine (solvent reactant) and 2.0 parts (0.064 mol/mol $C_2H_4$) of Fe(CO)$_5$ was placed in a 300 ml stainless steel autoclave. The autoclave was pressured with 300 psig of ethylene. A total of 6.6 parts of triethylamine and 0.4 parts of monoethylamine were obtained corresponding to a conversion of 28.2% and a combined yield of 100% (based on diethylamine).

EXAMPLE 6

A mixture of 100 parts of toluene (inert solvent), 9.1 parts of diethylamine and 0.97 parts (0.04 mol/mol $C_2H_4$) Fe(butadiene)(CO)$_3$ were placed in a 300 ml stainless steel autoclave. The autoclave was purged with ethylene and pressured with ethylene to 200 psig. A total of 1.6 parts of triethylamine were obtained corresponding to a conversion of 12.8% and a yield of 100% (based on diethylamine).

EXAMPLE 7

A mixture of 100 parts of 1,4-dioxane (inert solvent), 9.1 parts of diethylamine and 0.98 parts (0.04 mol/mol $C_2H_4$) of Fe(CO)$_5$ were placed in a 300 ml stainless steel autoclave. The autoclave was purged with ethylene and pressurized with ethylene to 200 psig. A total of 1.8 parts of triethylamine were obtained corresponding to a conversion of 14.1% and a yield of 93% (based on diethylamine).

EXAMPLE 8

A mixture of 55 parts of ammonia (solvent reactant) and 0.98 parts (0.035 mol/mol $C_2H_4$) of Fe(CO)$_5$ were placed in a 300 ml stainless steel autoclave. The autoclave was pressured with 200 psig of ethylene. The mixture was heated at 120° C. for 5 hrs. The autoclave was chilled with a dry ice/acetone bath opened to the atmosphere and 100 parts of toluene added. After warming to room temperature with the resultant evaporation of excess ammonia, the mixture was analyzed by gas liquid chromatography and was found to contain monoethylamine, diethylamine and triethylamine.

EXAMPLE 9

A mixture of 10 parts of ammonia (solvent reagent), 1.96 parts of Fe(CO)$_5$, 2.02 parts of tri-n-butylphosphine (combined catalyst=0.04 mol/mol of $C_4H_8$) and 14 parts of isobutylene were placed in a 300 ml stainless steel autoclave. The autoclave was sealed and heated to 170° C. for 5 hrs. The autoclave was chilled with a dry ice/acetone bath, opened to the atmosphere and 50 parts of toluene added. After warming to room temperature with the resultant evaporation of excess ammonia and isobutylene, the mixture was analyzed by gas liquid chromatography and was found to contain isobutylamine.

EXAMPLE 10

A mixture of 21.3 parts of piperidine (solvent reactant, 1.96 parts of $Fe(CO)_5$ and 0.27 parts of mercuric chloride (combined catalyst=0.063 mol/mol of $C_2H_4$) were placed in a 300 ml stainless steel autoclave. The autoclave was purged with ethylene and pressurized with ethylene to 300 psig. A total of 2.1 parts of N-ethylpiperidine were obtained corresponding to a conversion of 8% and a yield of 99% (based on piperidine).

EXAMPLE 11

A mixture of 18.3 parts of anhydrous diethylamine (solvent reactant), 2.0 parts of $Fe(CO)_5$ 3.1 parts of triphenylphosphite (combined catalyst=0.063 mol/mol of $C_2H_4$) were placed in a 300 ml stainless steel autoclave. The autoclave was pressured with 300 psig of ethylene. A total of 10.5 parts of triethylamine and 0.6 parts of monoethylamine were obtained corresponding to a conversion of 47.4% and a combined yield of 98.4% (based on diethylamine).

EXAMPLE 12

A mixture of 23.3 parts of anhydrous aniline (solvent reactant) 2.0 parts $Fe(CO)_5$ and 3.1 parts of triphenylphosphite (combined catalyst=0.064 mol/mol of $C_2H_4$) were placed in a 300 ml stainless steel autoclave. The autoclave was pressured with 300 psig of ethylene. A total of 3 parts of N-ethyl aniline, 1 part 2-methylquinoline, 1 part diethyl aniline, 0.5 parts 2-(1-butenyl)aniline and 0.25 parts of N-ethyl toluidine were obtained corresponding to a conversion of 17.3% and a combined yield of 100% (based on aniline).

What is claimed is:

1. A process for the production of aliphatic and aromatic amines which comprises reacting in a liquid phase an olefin having from 2 to 18 carbon atoms with either ammonia, a lower primary amine or a lower secondary amine in the presence of a catalyst at a temperature of 100° C. to 250° C., and at a pressure of at least autogenous and up to 12,000 psig whereby an N—H bond is added across the double bond of the olefin, said catalyst being selected from the class consisting of an iron salt and a coordination compound of iron.

2. The process of claim 1 wherein the olefin is a $C_2$–$C_4$ alkyl $\alpha$ olefin.

3. The process of claim 2 wherein ammonia is reacted with said olefin.

4. The process of claim 2 wherein a di $C_1$–$C_2$ alkylamine is reacted with said olefin.

5. The process of claim 2 wherein piperidine is reacted with said olefin.

6. The process of claim 2 wherein aniline is reacted with said olefin.

7. The process of claim 3, 4, 5 or 6 wherein the temperature is 100°–190° C. and the pressure is 200–1500 psig.

8. The process of claim 7 wherein the liquid phase comprises an inert solvent in which the reactant and catalyst are dissolved, said solvent selected from the group consisting of
   (a) a saturated aliphatic hydrocarbon,
   (b) an aromatic hydrocarbon,
   (c) an ether,
   (d) a saturated aliphatic alcohol, and
   (e) an amine.

9. The process of claim 7 wherein the catalyst is a coordination compound of iron selected from the group consisting of
   $Fe(CO)_5$,
   $FeHg(CO)_4$,
   $Fe(CO)_4(triphenylphosphite)$,
   $Fe(CO)_4(tri-n-butylphosphine)$ and
   $Fe(butadiene)(CO)_3$.

* * * * *